United States Patent
Kunnen et al.

(10) Patent No.: US 8,183,401 B2
(45) Date of Patent: May 22, 2012

(54) EXEMESTANE AND ITS INTERMEDIATES AND METHODS OF MAKING THE SAME

(75) Inventors: Kevin Kunnen, Plymouth, IN (US); Nathan W. Stehle, St. Charles, IL (US); Scot W. Weis, Milwaukee, WI (US); John M. Pascone, Grafton, WI (US); Richard J Pariza, Zion, IL (US); Scott G. Van Ornum, Jackson, WI (US); Paul Zizelman, Grafton, WI (US)

(73) Assignee: Cedarburg Pharmaceuticals, Inc., Grafton, WI (US)

( * ) Notice: Subject to any disclaimer, the term of this patent is extended or adjusted under 35 U.S.C. 154(b) by 1040 days.

(21) Appl. No.: 10/586,237

(22) PCT Filed: Jan. 14, 2005

(86) PCT No.: PCT/US2005/001248
§ 371 (c)(1),
(2), (4) Date: Jun. 6, 2008

(87) PCT Pub. No.: WO2005/070951
PCT Pub. Date: Aug. 4, 2005

(65) Prior Publication Data
US 2008/0234505 A1     Sep. 25, 2008

Related U.S. Application Data

(60) Provisional application No. 60/536,944, filed on Jan. 16, 2004.

(51) Int. Cl.
*C07J 1/00* (2006.01)
*A61K 31/56* (2006.01)
(52) U.S. Cl. ............... 552/526; 552/640; 514/177
(58) Field of Classification Search ........... 514/177; 552/526, 640
See application file for complete search history.

(56) References Cited

U.S. PATENT DOCUMENTS

| | | | |
|---|---|---|---|
| 2,805,231 A | 9/1957 | Dodson et al. | 260/397.4 |
| 3,274,176 A | 9/1966 | Dube | 260/239.5 |
| 3,404,150 A | 10/1968 | Halpern | 260/239.55 |
| 3,634,469 A | 1/1972 | Nysted | 260/397.5 |
| 3,850,911 A | 11/1974 | Hughes | 260/239.5 |
| 4,474,701 A | 10/1984 | Teichmuller et al. | 260/397.3 |
| 4,537,722 A | 8/1985 | Stamvik et al. | 260/397.4 |
| 4,808,616 A | 2/1989 | Buzzetti et al. | 514/177 |
| 4,822,528 A | 4/1989 | Colombo et al. | 260/397.3 |
| 4,824,830 A * | 4/1989 | Buzzetti et al. | 514/177 |
| 4,876,045 A * | 10/1989 | Longo et al. | 552/526 |
| 4,904,650 A | 2/1990 | Buzzetti et al. | 514/177 |
| 4,925,834 A | 5/1990 | Bohlmann et al. | 514/177 |
| 4,990,635 A | 2/1991 | Longo et al. | 552/526 |
| 5,227,375 A | 7/1993 | Labrie et al. | 514/172 |
| 7,846,918 B2 * | 12/2010 | Pariza et al. | 514/177 |
| 2008/0275259 A1 * | 11/2008 | Chen et al. | 552/526 |

FOREIGN PATENT DOCUMENTS

DE      258820 A1      8/1988

OTHER PUBLICATIONS

International Search Report and Written Opinion Under Date of Mailing of Apr. 26, 2005, in connection with International Patent Application No. PCT/US2005/001248.

* cited by examiner

*Primary Examiner* — Sabiha Qazi
(74) *Attorney, Agent, or Firm* — Quarles & Brady LLP

(57) ABSTRACT

A method is provided for preparing an aromatase inhibitor of formula (I) wherein each of $R_1$, $R_2$, $R_3$, $R_4$, independently, is hydrogen, halogen or $C_1$-$C_6$ alkyl. In one form, the aromatase inhibitor is exemestane wherein each of $R_1$, $R_2$, $R_3$, $R_4$ is hydrogen. In the method, a compound of formula (II) wherein $R_1$, $R_2$, $R_3$, $R_4$ are as defined above and R is alkylene, is reacted with a deprotonating agent and a compound of the formula $R_5SO_2X$ wherein $R_5$ is $C_1$-$C_5$ alkyl and X is halogen so as to obtain a compound of formula (III) wherein $R_1$, $R_2$, $R_3$, $R_4$, $R_5$ are as defined above. The compound of Formula (III) is then reacted with a base to form an aromatase inhibitor of formula (I).

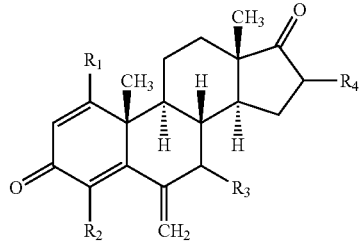
(I)
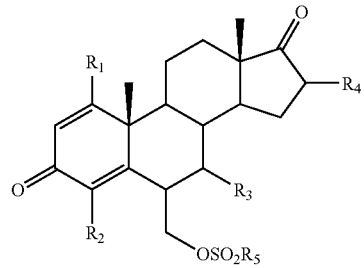
-continued
(III)
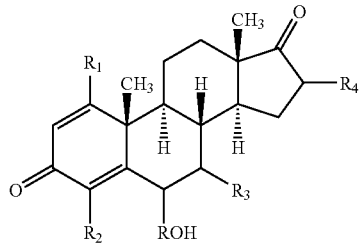
(II)
16 Claims, 2 Drawing Sheets

EXEMESTANE AND ITS INTERMEDIATES AND METHODS OF MAKING THE SAME

CROSS-REFERENCES TO RELATED APPLICATIONS

This application is a 371 of PCT/US2005/001248 filed Jan. 14, 2005 which claims priority from U.S. Provisional Patent Application No. 60/536,944 filed Jan. 16, 2004.

STATEMENT REGARDING FEDERALLY SPONSORED RESEARCH

Not Applicable.

BACKGROUND OF THE INVENTION

1. Field of the Invention

The invention relates to methods of making aromatase inhibitors such as exemestane and its intermediates.

2. Description of the Related Art

Product information available on-line from the U.S. Food and Drug Administration describes exemestane as an irreversible, steroidal aromatase inactivator. Exemestane (which is sold as Aromasin®) is chemically described as 6-methylenandrosta-1,4-diene-3,17-dione. Its molecular formula is $C_{20}H_{24}O_2$ and its structural formula is as follows:

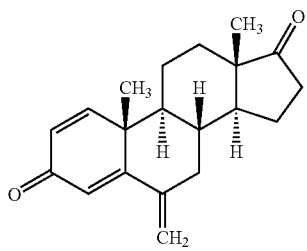

The clinical pharmacology in this exemestane product information states that the mechanism of action for breast cancer cell growth may be estrogen-dependent. Aromatase is described as the principal enzyme that converts androgens to estrogens both in pre- and postmenopausal women. It is reported that the principal source of circulating estrogens in postmenopausal women is from conversion of adrenal and ovarian androgens (androstenedione and testosterone) to estrogens (estrone and estradiol) by the aromatase enzyme. Estrogen deprivation through aromatase inhibition is described as an effective and selective treatment for some postmenopausal patients with hormone-dependent breast cancer. Exemestane as an irreversible, steroidal aromatase inactivator that acts as a false substrate for the aromatase enzyme, and is processed to an intermediate that binds irreversibly to the active site of the enzyme causing its inactivation. Exemestane lowers circulating estrogen concentrations in postmenopausal women thereby providing a treatment for some postmenopausal patients with hormone-dependent breast cancer.

U.S. Pat. Nos. 4,808,616, and 4,904,650 describe 6-alkylidenandrosta-1,4-diene-3,17-dione derivatives, such as exemestane, and methods of making them. U.S. Pat. No. 4,876,045 teaches a method of preparing 6-methylene derivatives of androsta-1,4-diene-3,17-diones by reacting a 17-hydroxy precursor with formaldehyde and an amine, and then oxidizing the resulting compound. U.S. Pat. No. 4,990,635 teaches a process for making 6-methylene derivatives of androsta-1,4-diene-3,17-diones by reacting androsta-3,5-diene-17-one with formaldehyde and an amine, and then dehydrogenating the resulting compound.

The preparation of intermediates that may be useful in preparing exemestane is also described in the literature. In U.S. Pat. No. 3,274,176, there is described a process for making 1,3-dipyrrolidyl-$\Delta^{3,5}$-androstadiene-17-one in which $\Delta^{1,4}$-androstadiene-3,17-dione is refluxed with pyrrolidine and the residue is crystallized in methanol to obtain 1,3-dipyrrolidyl-$\Delta^{3,5}$-androstadiene-17-one. In German patent DD 258820, 6-hydroxymethyl-androsta-1,4-diene-3,17-dione is prepared from androsta-1,4-diene-3,17-dione via 1,3-dipyrrolidinoandrosta-3,5-dien-17-one. A solution of 1,3-dipyrrolidinoandrosta-3,5-dien-17-one in benzene-ethanol is stirred with aqueous formaldehyde (HCHO) until the reaction is complete.

Although various methods and intermediates for preparing aromatase inhibitors such as exemestane have been described in the art, there is a continuing need for improved methods and intermediates for preparing aromatase inhibitors such as exemestane, particularly in commercial quantities with high yield and high purity.

SUMMARY OF THE INVENTION

The foregoing needs are met by a method according to the invention for preparing an aromatase inhibitor of formula (I)

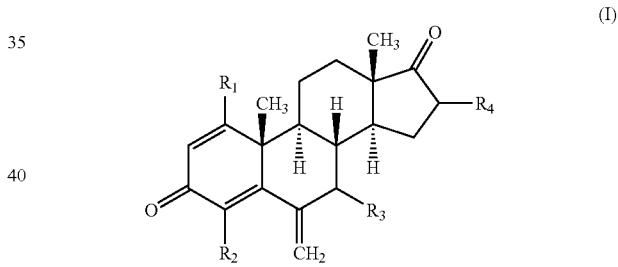

wherein each of $R_1$, $R_2$, $R_3$, $R_4$, independently, is hydrogen, halogen or $C_1$-$C_6$ alkyl. In one form, the aromatase inhibitor is exemestane wherein each of $R_1$, $R_2$, $R_3$, $R_4$ is hydrogen. In the method, a compound of formula (II)

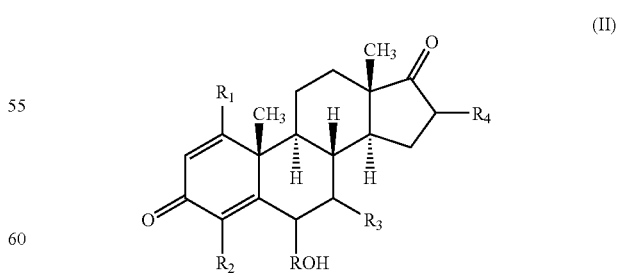

wherein $R_1$, $R_2$, $R_3$, $R_4$ are as defined above and R is alkylene, is reacted with a deprotonating agent and a compound of the formula $R_5SO_2X$ wherein $R_5$ is $C_1$-$C_5$ alkyl and X is halogen so as to obtain a compound of formula (III)

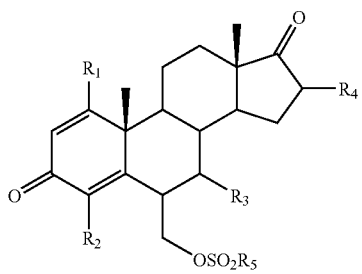

(III)

wherein $R_1$, $R_2$, $R_3$, $R_4$, $R_5$ are as defined above. The compound of Formula (III) is then reacted with a base to form an aromatase inhibitor of formula (I). Preferably, the compound of formula (III) is reacted with the base in a solvent.

In another aspect of the invention, there is provided a method for preparing exemestane which has the formula

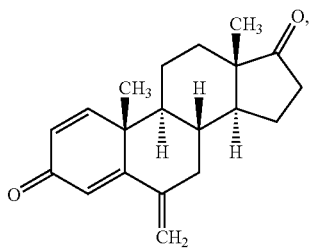

wherein a compound of formula (V)

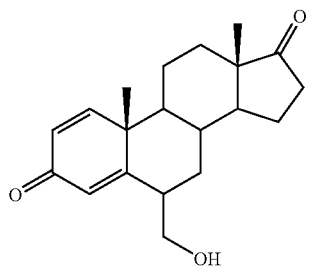

(V)

is reacted with a deprotonating agent and a compound of the formula $R_5SO_2X$ wherein $R_5$ is $C_1$-$C_5$ alkyl and X is halogen so as to obtain a compound of formula (VI)

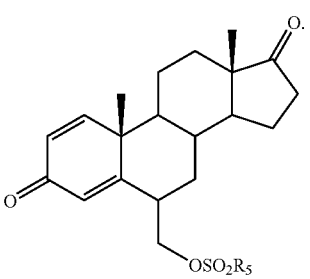

(VI)

The compound of formula (VI) is then reacted with a base in a solvent. In this aspect of the invention, $R_5$ is preferably methyl and X is preferably chlorine. In one version of the invention, the base may be an alkali metal hydroxide, and the solvent may be an alkanol.

In yet another aspect of the invention, there is provided an intermediate useful in preparing an aromatase inhibitor such as exemestane. The intermediate is a compound of the formula (IV):

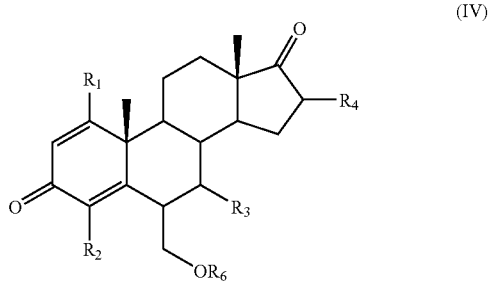

(IV)

wherein each of $R_1$, $R_2$, $R_3$, $R_4$, independently, is hydrogen, halogen or $C_1$-$C_6$ alkyl, and $R_6$ is a substituent (one or more atoms) other than hydrogen. In this intermediate, each of $R_1$, $R_2$, $R_3$, $R_4$ is preferably hydrogen. and $R_6$ is preferably $SO_2R_5$ wherein $R_5$ is $C_1$-$C_5$ alkyl. Most preferably, $R_5$ is methyl.

It is an advantage of the invention to provide improved methods and intermediates for preparing aromatase inhibitors such as exemestane in high purity and high yield, particularly in commercial quantities.

These and other features, aspects, and advantages of the present invention will become better understood upon consideration of the following detailed description, drawings, and appended claims.

DETAILED DESCRIPTION OF THE INVENTION

This invention provides a method for preparing an aromatase inhibitor of formula (I).

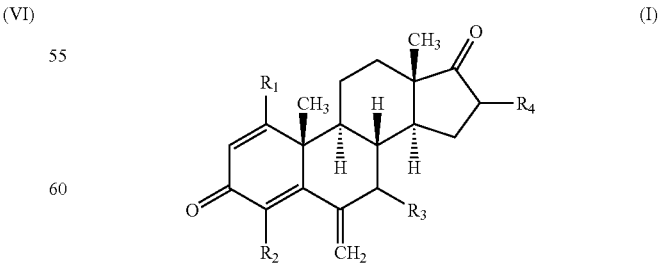

(I)

wherein each of $R_1$, $R_2$, $R_3$, $R_4$, independently, is hydrogen, halogen or $C_1$-$C_6$ alkyl. In one form, the aromatase inhibitor is exemestane wherein each of $R_1$, $R_2$, $R_3$, $R_4$ is hydrogen.

In an example method according to the invention wherein the aromatase inhibitor is exemestane, a compound of formula (V)

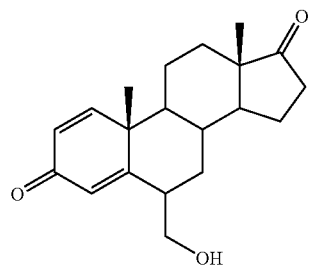

(V)

is reacted with a deprotonating agent and a compound of the formula $R_5SO_2X$ wherein $R_5$ is $C_1$-$C_5$ alkyl and X is halogen so as to obtain a compound of formula (VI)

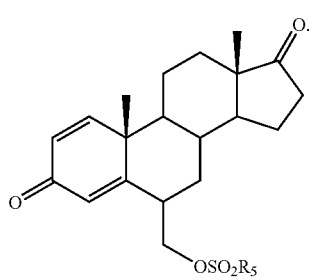

(VI)

The compound of formula (VI) is then reacted with a base in a solvent to produce exemestane.

Figure 4:
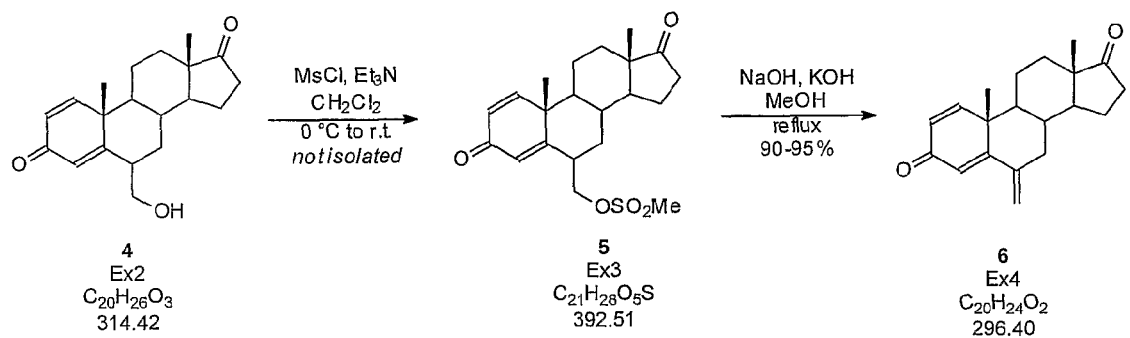
FIG. 4 shows a reaction scheme according to the invention for the preparation of exemestane (EX-4) from 6-hydroxymethyl-androsta-1,4-diene-3,17-dione (EX-2).

One version of this method of the invention is shown in FIG. 4. The compound of formula (V) is labeled as 4 (EX-2) in FIG. 4. The compound of formula (V) is treated with a deprotonating agent and a compound of the formula $R_5SO_2X$, wherein $R_5$ is $C_1$-$C_5$ alkyl and X is halogen, in a solvent such as dichloromethane. Temperatures in the range of 0-35° C. work well. In the version of the invention shown in FIG. 4, an example deprotonating agent is triethylamine ($Et_3N$). It is contemplated that other amines are suitable deprotonating agents including other tertiary amines and other trialkylamines. The compound of the formula $R_5SO_2X$ in FIG. 4 is methanesulfonyl chloride (MsCl). Other alkanesulfonyl halides would also be suitable. The compound of formula (VI) above, wherein $R_5$ is methyl, is then formed as intermediate 5 (Ex3) in FIG. 4.

Still referring to FIG. 4, the reaction mixture is washed with water, diluted with a solvent (methanol (MeOH) is the example in FIG. 4) and treated with a base (aqueous potassium hydroxide (KOH) or sodium hydroxide (NaOH) are the examples in FIG. 4). Suitable solvents include, without limitation, alkanols, and suitable bases include, without limitation, alkali metal hydroxides. The methylene chloride is removed via distillation and the elimination progresses concurrently. On reaction completion, water is added to complete product precipitation and the solution cooled. The product is isolated, washed with methanol/water, water, dried and then recrystallized from ACN/water. The exemestane (labeled 6 and Ex4 in FIG. 4) yields after drying are typically 80-90% with purities of 99.5+% by HPLC area analysis. Thus, the reaction scheme of FIG. 4 shows a method and an intermediate 5 useful in forming exemestane in high yields with high purity.

The reaction scheme of FIG. 4 can also be modified to form other aromatase inhibitors of formula (I).

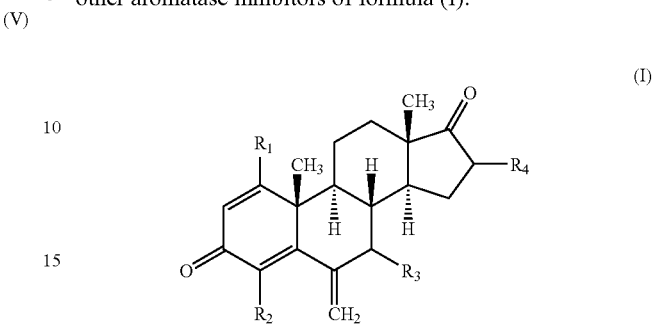

(I)

wherein each of $R_1$, $R_2$, $R_3$, $R_4$, independently, is hydrogen, halogen or $C_1$-$C_6$ alkyl with suitable protection of substituting groups $R_1$, $R_2$, $R_3$, $R_4$ in the reaction scheme.

EXAMPLES

The following Examples have been presented in order to further illustrate the invention and are not intended to limit the invention in any way.

Example 1

Identification of Major Impurity in ADD

Figure 2:
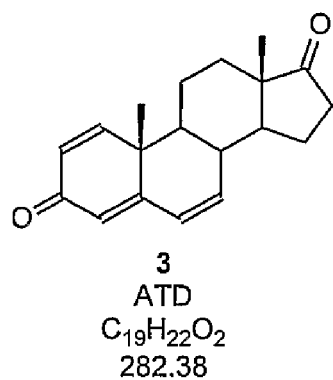
FIG. 2 shows the structure of androsta-1,4,6-trien-3,17-dione (ATD).

The (+)-androsta-1,4-diene-3,17-dione (ADD) supplied for the process contained an impurity that was identified as androsta-1,4,6-trien-3,17-dione (ATD) via LC-MS and comparison to authentic ATD (see FIG. 2). This impurity is presumably formed via over-oxidation of the desired ADD during the production process.

Example 2

Preparation of 1,3-dipyrrolidinoandrosta-3,5-diene-17-one (EX-1) from (+)-androsta-1,4-diene-3,17-dione (ADD)

Figure 1:
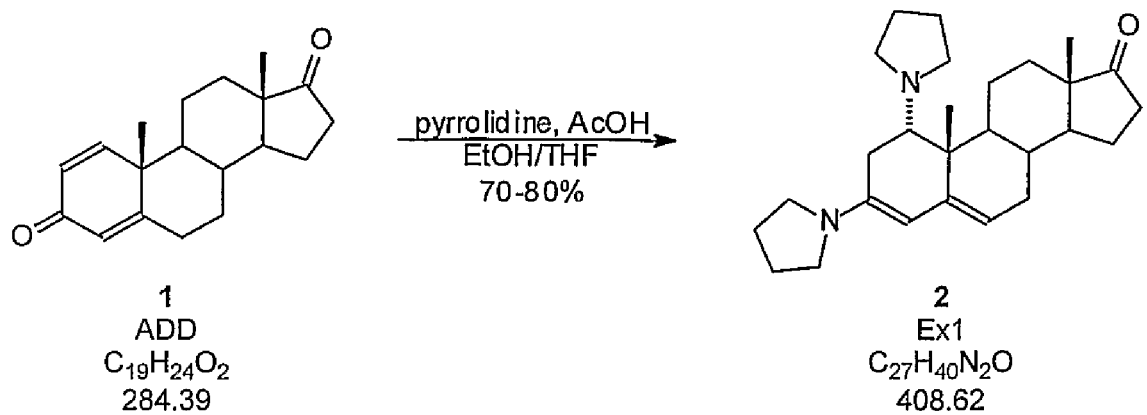
FIG. 1 shows a reaction scheme for the preparation of 1,3-dipyrrolidinoandrosta-3,5-diene-17-one (EX-1) from (+)-androsta-1,4-diene-3,17-dione (ADD).

One set of conditions utilizes (+)-androsta-1,4-diene-3,17-dione (ADD), 12.2 equivalents pyrrolidine, catalytic acetic acid, denatured ethanol (95/5 ethanol/methanol) and 6-7% tetrahydrofuran (volume basis of total volume of ethanol and pyrrolidine) with heating to 30-40° C. for a minimum of 16 hours. Once the ADD content is less than 3% by HPLC area, becomes static or EX-1 begins to revert to ADD, the reaction mixture is cooled to 5±5° C., collected and washed with cold denatured ethanol. Yields are typically 70-80% on a dry basis with purities typically 90-95% by HPLC area percent. The reaction scheme is shown in FIG. 1.

The ranging studies for the preparation of 1,3-dipyrrolidinoandrosta-3,5-diene-17-one (EX-1) included the following: A. Effect of purity of ADD (by weight percent analysis) on product yield and quality; B. Reaction temperature; C. Pyrrolidine stoichiometry; D. Amount of THF; E. Acetic acid stoichiometry; F. Temperature for isolation of EX-1; G. Hold time for cooled slurry of EX-1 prior to isolation; H. Solvent for the preparation of EX-1 and subsequent washing(s); and I. Drying temperature for isolated EX-1.

Using ADD with a weight percent analysis of 92% afforded EX-1 in 73% isolated yield and a HPLC purity of 95% area. By comparison, 99.5% weight ADD (available from Aldrich) gave 82% EX-1 with a purity of 95% area by HPLC analysis.

With comparable purities of EX-1 produced with ADD that was 92 or 98 weight percent ADD, the fate of the ATD (major impurity present in ADD) was examined. Two experiments were performed: one using filtrates from EX-1 isolation (in ethanol) and the second with a slurry of isolated EX-1 in ethanol. Each sample was treated with acetonitrile, methanol and excess aqueous KOH. After stirring at ambient temperature for 23 hours, most if not all, EX-1 was consumed in both cases. Hydrolysis of EX-1 filtrates produced a solution that was enriched in ATD relative to ADD. Solid EX-1 in ethanol produces ADD with 0.20% area of ATD present after basic hydrolysis.

Reaction temperature for the process ranges from 30° to 40° C., and the reaction can be run at a lower temperature of 20° C. but requires a longer time for completion. Under standard conditions, the preparation of EX-1 from ADD typically takes approximately 16-20 hours. The preparation of EX-1 at 20° C. took 30 hours until ADD consumption leveled off and the reaction was considered complete. The yield was 74% with a purity of 95% by HPLC area percent. Synthesis of EX-1 at 50-60° C. provided the product in 84% isolated yield with a purity of 86% area by HPLC, which meets the specified purity level of >80%.

Extension of the operation ranges for pyrrolidine stoichiometry from 11.4 to 13.1 equivalents (based on amount of ADD) to 9 to 15 equivalents proved to be acceptable for producing EX-1 of very good quality (>90% by HPLC area). The preparation of EX-1 with nine equivalents of pyrrolidine provided the desired bis-enamine EX-1 in 77% isolated yield with a purity of 94% by HPLC area percent. On the higher end of the verification range, 15 equivalents of pyrrolidine afforded EX-1 in 65% isolated yield with a purity of 93% area by HPLC area percent.

Tetrahydrofuran is employed in the EX-1 preparation process to provide a stirrable slurry of EX-1 on crystallization of the desired product after seeding and sufficient reaction progress. The working range for the process is 6.6 to 7.2% of the combined volume of ethanol and pyrrolidine. Using EX-2 and 10% THF provided stirrable mixtures on seeding and subsequent reaction advancement, which is one criterion for an acceptable range in this case. Both percentages of THF afforded the desired product in 72% isolated yield and purities of 94% area and 96% by HPLC area percent respectively.

Acetic acid is used as a catalyst in the formation of EX-1 with typically 0.10 to 0.11 equivalents (relative to ADD) of acid being used. The lower end of the acetic acid ratio, 0.05 equivalents, provided EX-1 in 45% isolated yield with a purity of 95% by HPLC area percent. The higher end, 0.50 equivalents, afforded the desired product in 70% isolated yield and purity of 95% area by HPLC analysis.

Temperature for isolation of 1,3-dipyrrolidinoandrosta-3,5-diene-17-one (EX-1) at <0° C. or 15° C. had no observable impact on yield and product purity. This verification range study determined that the process range of 5±5° C. is acceptable, but that slightly warmer or colder temperatures are tolerated.

The process to prepare EX-1 used thus far employed ethanol as the solvent, which has provided suitable material for use in the exemestane process. Two of the more frequently used, commercially available denatured ethanol mixtures were examined in an effort to reduce costs (associated with taxes for 100% ethanol). Use of 95/5 ethanol/isopropanol afforded EX-1 in 64% isolated yield with a purity of 94% by HPLC area. With 95/5 ethanol/methanol as the reaction solvent, EX-1 was obtained in 73% isolated yield with a purity of 95% by HPLC area percent. In both cases, the reaction mixture was a stirrable slurry with no problems observed during isolation of the solid product.

Drying of EX-1 at ambient temperature was not investigated as the expectation was that it would provide adequate drying, only at much longer times, which would be inefficient. The operating range for the process is 27 to 43° C., so an upper temperature for verification of 55° C. was selected. The wet cake of EX-1 was placed into a vacuum oven preheated to 55° C. Dried EX-1 was obtained in 70% isolated yield with a purity of 93% area by HPLC analysis. The ADD content was at 1.5% area, indicating that partial hydrolysis had likely occurred on drying as the wet cake had an ADD content of 0.15% by HPLC analysis.

Hold times for crystallization of EX-1 on reaction workup have been established for a minimum of three hours up to 16 hours. Three hours is the time used for hold at 5±5° C. Holding at this temperature for 16 hours provided the desired product in 74% isolated yield with a purity of 95% area by HPLC.

Example 2

Discussion

Utilizing higher purity ADD does not appear to noticeably impact the quality of 1,3-dipyrrolidinoandrosta-3,5-diene-17-one (EX-1) produced. Unless otherwise noted, the ranging studies were conducted with ADD that was found to be 92% weight. The only benefit observed was an increase in yield of isolated EX-1, which increased to 82% from the typical 70 to 75% observed on lab scale. One benefit would then be one of a moderately increased throughput of ADD to exemestane as purity of EX-1 obtained were very similar. The purities of EX-1 produced was usually 93 to 95% area by HPLC analysis during the course of the ranging studies, and using higher quality ADD produced EX-1 with a purity of 95% area by HPLC analysis.

Based on the hydrolysis results from treatment of two EX-1 samples with aqueous potassium hydroxide, ATD is converted to product(s) that are removed in the filtrates. ATD itself is not found to significant extent (>0.50% by HPLC area) in the filtrates prior to hydrolysis. The presence of ATD in the hydrolyzed filtrates and lack of significant amount (>1%) in the hydrolyzed EX-1 demonstrates that there are very little ATD and related products carried forward in the process.

Preparing EX-1 at warmer temperatures leads to a reduced conversion of ADD to EX-1, but does provide product of acceptable quality. The trend of improved conversions at lower temperatures was noted very early in the process development phase of the exemestane project.

Varying the ratio of pyrrolidine produced the expected results of impacting the yield of isolated bis-enamine EX-1 but not the quality. Using a lower amount of pyrrolidine resulted in a slight increase in yield (approximately 5%) with purity comparable to that obtained with the standard conditions. Increasing the amount of pyrrolidine to 15 equivalents lead to a decreased isolated yield (about 8% decrease) but comparable and acceptable purity of 93% area by HPLC.

Changes in the THF ratio were acceptable and provided EX-1 of good quality (>90% area EX-1 by HPLC). Variance in the amount of acetic acid was not expected have a significant impact on the process due to the large (>12 equivalents) amount of pyrrolidine present and observed results supported this preliminary hypothesis.

Utilization of a denatured ethanol mixture was anticipated to be allowed for use in the EX-1 process and that was confirmed by the use of ethanol/isopropanol and ethanol/methanol. The later was expected to provide a yield comparable or better than the process employing ethanol alone. The working hypothesis was that since the previous process for preparing EX-1 utilized water for aiding in additional precipitation of EX-1, then a more polar solvent mixture should provide a better yield of EX-1 over a less polar one. The data obtained indeed show a lower yield using the less polar ethanol/isopropanol mixture versus the more polar ethanol/methanol mixture. The former provided EX-1 in 64% isolated yield and the lafter in 73% isolated yield. Both the ethanol/methanol and ethanol/isopropanol solvent mixtures for EX-1 synthesis were similar in quality of EX-1 produced, if not identical to the one using ethanol alone.

Drying EX-1 at 55° C. provides material with less than <2% area (by HPLC) ADD, but the higher ADD content than is typically observed on lab scale is due to drying in a hot oven with solvent and pyrrolidine remaining. Subsequent experiments indicated that by ramping the drying and holding the wet cake in an amber container better preserves the quality of EX-1 obtained.

An observation that the product dried in clear containers was usually darker in color than the EX-1 dried in amber bottles. This result indicates that the product is light sensitive, especially the wet cake as the discoloration occurs the most on drying (qualitative assessment).

Example 2

Conclusions

The preparation of 1,3-dipyrrolidinoandrosta-3,5-diene-17-one (EX-1) from (+)-androsta-1,4-diene-3,17-dione (ADD) has undergone considerable optimization to produce a product of consistent quality. One of the hurdles overcome was maintaining a stirrable reaction mixture as the product will crystallize out over time. One of the methods used to control reaction mixture was seeding the solution after several hours of heating which led to a gradual, more controlled crystallization as opposed to a rapid solidification that causes stirring to suddenly cease. Another important modification was the addition of a small percentage of tetrahydrofuran, which has the effect of thinning the heterogeneous mixture enough so as to allow for good stirring.

The impurity contained in (+)-androsta-1,4-diene-3,17-dione (ADD) was identified to be 1,4,6-androstatrien-3,17-dione (ATD) and experiments demonstrated that its presence does not adversely affect quality of EX-1 isolated. The product(s) resulting from the triene are very efficiently removed in the isolation and washing of EX-1. As a result, the triene and related materials are not carried forward in the process.

Development work has established that there is a good amount of tolerance within the numerous operating parameters for the EX-1 process. The observations and results observed have provided the data in terms of yields and purities. The established process is robust and very reproducible and should lend itself well to validation.

Example 3

Preparation of 6-hydroxymethyl-androsta-1,4-diene-3,17-dione (EX-2) from 1,3-dipyrrolidinoandrosta-3,5-diene-17-one (EX-1)

Figure 3:
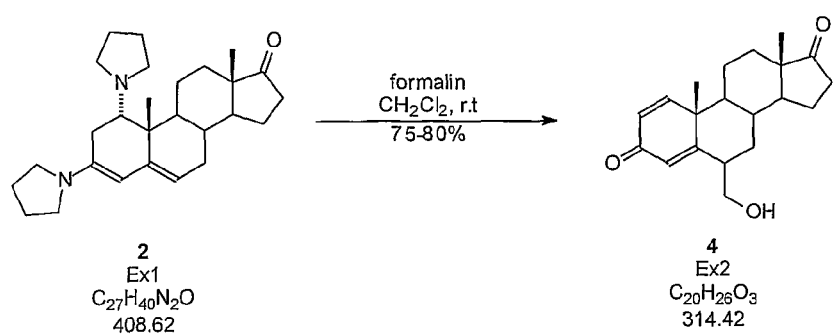
FIG. 3 shows a reaction scheme for the preparation of 6-hydroxymethyl-androsta-1,4-diene-3,17-dione (EX-2) from 1,3-dipyrrolidinoandrosta-3,5-diene-17-one (EX-1).

One set of conditions for the preparation employ 1 equivalent 1,3-dipyrrolidinoandrosta-3,5-diene-17-one (EX-1) and 2.6 equivalents formalin (formaldehyde) in 10 mL dichloromethane/g of EX-1 at room temperature. Workup consists of acidification of the reaction mixture to a pH of about 2, dilution with 2% sulfuric acid (aqueous, volume/volume basis) and removal of the organic layer which is then washed with 2% sulfuric acid (vol/vol) and 1:1 water/brine. Solvent exchange into toluene (approximately 10 mL/g theory EX-2) is then carried out and the product crystallizes as toluene exchange transpires. The product is collected, washed and dried to provide 6-hydroxymethyl-androsta-1,4-diene-3,17-dione (EX-2) in yields of typically 75-80%. Purity is usually 96% or greater by HPLC area percent. A reaction scheme is shown in FIG. 3.

The ranges investigated for the verification included: A. stoichiometry of formalin; B. reaction duration; C. pH of the acidified reaction mixture; D. amount of toluene for solvent exchange and crystallization; E. endpoint of the distillation as determined by specific gravity of the distillate; and F. drying temperature for the isolated product.

With higher and lower ratios of formalin to EX-1 isolated yields were lower but purities comparable to results from standard conditions (about 98-99% by HPLC area). Preparing EX-2 using 2.0 equivalents of formalin provided the desired product in 65% isolated yield with a purity of 99.3% by HPLC area. The upper portion of the range used 3.0 equivalents formalin and this amount afforded EX-2 in 67% isolated yield with a purity of 98.9% area by HPLC analysis.

Reaction duration is important as impurities have been observed to increase as the reaction times lengthen. The reaction is rapid, and is complete (as determined by consumption of enamine EX-1 by HPLC analysis) within 15 minutes after the addition of formalin to the vigorously stirred dichloromethane solution of EX-1. This process provided alcohol EX-2 in 76% isolated yield with a purity of 98.6% by HPLC area. Allowing the reaction to continue for three hours gave EX-2 in 85% yield with a purity of 98.3% by HPLC area.

Initial acidification of the reaction mixture once EX-1 has been consumed is also important in providing better yields of EX-2. Workup of the EX-2 reaction mixture is carried out by treatment with 15% sulfuric acid (volume/volume) until the pH is about 2. Bringing the pH of the reaction mixture to a value of <1 gave EX-2 in 78% isolated yield with a purity of 99.2% by HPLC area. Acidification to a pH of 3 gave a yield of 75% with a purity of 99.3% area by HPLC. Allowing the pH to be 3.7 on workup afforded the alcohol EX-2 in a very slightly lower yield of 71% and a comparable purity of 99.2% HPLC area.

Exchange of the dried dichloromethane solution of EX-2 into toluene provides the product as a solid which is collected, washed and dried. Standard conditions use a toluene loading of 11-13 mL per gram of theoretical yield of EX-2. Utilizing 7 mL/g of toluene gave the alcohol EX-2 in 76% yield on drying with a purity of 98.6%. This result represents a slight decrease in purity and no significant change in isolated yield versus standard conditions. With 15 mL/g toluene, EX-2 was afforded in 54% isolated yield and an excellent purity of 99.4% area by HPLC.

In order to easily monitor the endpoint of the solvent exchange (via distillation) to remove dichloromethane, the specific gravity of the distillate at the end of the transfer should be monitored. Concentration of the EX-2 solution to dryness then slurrying in toluene provided a low distillate specific gravity which was measured to be 0.879 g/mL (toluene density is 0.889 g/mL). This synthesis gave EX-2 in 79% isolated yield with a slightly lower purity of 97.6% area by HPLC analysis. Carrying out the solvent exchange under standard conditions provided EX-2 in 67% isolated yield and a purity of 99.5%. In this case the specific gravity of the distillate was 1.02 g/mL, which is very close to the value of 1.04 g/mL used as the endpoint in the pilot plant. A higher value of 1.20 g/mL for the distillation specific gravity provides an acceptable batch of EX-2 in 69% isolated yield and a purity of 99.2% area by HPLC.

Drying at 55° C. or 72° C. each provided product that is of high purity. In the case of drying EX-2 at 55° C., the yield of the product is 75% with an area percent purity of 99.4. At 72° C., EX-2 was obtained in 80% isolated yield and a purity of 99.4% by HPLC analysis.

Example 3

Discussion

The reaction to prepare EX-2 provided the alcohol in excellent purity but slightly diminished yield using either 2.0 or 3.0 equivalents of formalin, indicating that a sizable stoichiometry range is allowed for in this process. Using the 2.6 equivalents currently specified will provide better yields and a product of excellent quality.

Keeping the reaction times short, i.e. one hour or less, is important to ensure that EX-2 is obtained in excellent purity. The reaction is typically complete within 15 minutes of formalin addition, so as a short a reaction time as is possible is preferred. Longer duration for the reaction eventually starts to degrade the purity of the isolated product, as evidenced by the three hour reaction to synthesize EX-2 which afforded material that was 98.3% purity by HPLC area.

Workup acidification from <1 to 3.7 was found to provide product of very good purity, but the yield appears to decline at a higher pH. The target pH in production has been less than 3, and this data supports that target for acidification.

Using less toluene than the approximately 11-13 mL/g of EX-2 used in the process was expected to provide comparable or better yield along with similar or lower purity than the standard conditions. The yield of 76% and slightly lower purity of 98.6% fit the initial hypothesis. Using a higher loading of toluene would be anticipated to provide lower recovery and excellent purity of EX-2, and this result was observed. The yield of EX-2 was 54% and the white solid has a purity of 99.4% by HPLC analysis.

Use of specific gravity of collected distillate for the solvent exchange provides a good marker for completion of the solid transfer as the sample is homogeneous and is not adversely affected by blow-by. By concentrating the crude solution of EX-2 to dryness, a comparable or higher recovery of product was expected as there would be little dichloromethane remaining. The purity could remain about the same or decrease as the product was not as likely to gradually crystallize and instead would be more precipitation occurring. When this process was executed, a yield of 79% and a decreased purity of 97.6% area by HPLC area percent was observed. The effect of a higher distillate specific gravity was a slight decrease in yield (69%) and an excellent purity of 99.2% HPLC area.

The purpose in drying at higher temperatures than the operating range was to demonstrate that the material is stable under those conditions and that product of very good to excellent purity could be obtained. The results obtained show that temperatures higher than the operating range of 30 to 40° C. are acceptable and have negligible impact on purity. The reason for the approach of examining a higher temperature is that drying on the lab scale is generally simpler and easier to perform than production scale drying.

Example 3

Conclusions

There are several key improvements that were made in the process to prepare 6-hydroxymethyl-androsta-1,4-diene-3,17-dione (EX-2) from 1,3-dipyrrolidinoandrosta-3,5-diene-17-one (EX-1). The use of dichloromethane as a reaction solvent, acidification to a pH of approximately 2 and the solvent transfer from dichloromethane into toluene to provide crystalline EX-2 are the significant improvements in the synthesis of EX-2. As a result of the considerable development work, the goal of delivering a scaleable process that produces excellent quality material with minimal to no ADD present was achieved. The presence of residual ADD had complicated the isolation of exemestane in previous campaigns.

The ranging studies carried out all indicated that the process as used is a reliable one that delivers high quality material on a consistent basis, as long as the process is kept within the established parameters. In certain cases, such as formalin stoichiometry and toluene ratios, the product yield will be impacted. In others like toluene ratio and distillate specific gravity, the purity can be very slightly impacted. These changes are not dramatic and strongly indicate that current operations using established ranges are well optimized.

Example 4

Preparation of Exemestane from 6-hydroxymethyl-androsta-1,4-diene-3,17-dione (EX-2)

Exemestane is prepared from EX-2 via a two step process by proceeding through the mesylate intermediate 5 (EX-3) of FIG. 4 (as a solution in dichloromethane), which is then converted to the final product exemestane. The mesylate 5 is not isolated but is used as provided after aqueous workup to afford exemestane in excellent yield and purity. Of course, intermediate 5 can be isolated if desired.

To prepare intermediate 5 of FIG. 4, a cold (5±5° C.) solution of 6-hydroxymethyl-androsta-1,4-diene-3,17-dione (EX-2) is treated with triethylamine and methanesulfonyl chloride. On consumption of EX-2 the reaction mixture is washed with water, diluted with methanol and treated with aqueous KOH. The methylene chloride is removed via distillation and the elimination progresses concurrently. Reaction progress is monitored until the EX-3 remaining level is <1% by HPLC analysis. On reaction completion, water is added to complete product precipitation and the solution cooled. The product is isolated, washed with 1:1 methanol/water, water, dried and then recrystallized from 1:1 ACN/water. The yields after drying are typically 80-90% with purities of 99.5+% by HPLC area analysis.

Parameters examined for the final step of the process were: A. Stoichiometry of triethylamine; B. Stoichiometry of methanesulfonyl chloride; C. Starting temperature of methanesulfonyl chloride addition; D. EX-2 remaining level by HPLC area percent; E. The methanol loading for the preparation of exemestane; F. Stoichiometry of potassium hydroxide; G. Temperature of the elimination reaction; H. EX-3 remaining level by HPLC area percent; I. Specific gravity of collected distillate at end of methylene chloride removal; J. Amount of water added for crystallization of exemestane; K. Hold time after water addition; L. Percent LOD of wet cake of exemestane prior to recrystallization; M. Amount of acetonitrile used for recrystallization; N. Amount of water used for recrystallization; O. Drying temperature for exemestane.

Investigation of the amount of triethylamine and methanesulfonyl chloride used to form the mesylate intermediate 5 demonstrated that as little as 1.1 equivalents of each (with respect to EX-2) provides complete (less than 1% area 4 by HPLC) conversion to EX-3. Use of 1.5 equivalents of methanesulfonyl chloride and 2.0 equivalents of triethylamine are also acceptable as demonstrated by ranging experiments. Ranging studies monitored the conversion EX-2 to EX-3 via HPLC area percent analysis and the EX-3 was not isolated or carried on to EX-4.

Examination of the temperature of methane sulfonyl chloride addition demonstrated that addition at either 0° C. or 35° C. (dichloromethane refluxes at 39 to 40° C.) provides excellent conversion of EX-2 to intermediate 5.

As much as 3% by weight of EX-2 is tolerated in the conversion of EX-3 to EX-4 as it is removed on crystallization of the EX-4 from the reaction mixture and subsequent recrystallization of EX-4. This experiment produced material that was 99.9% pure by HPLC area in an isolated yield of 83% after recrystallization.

Methanol loading studies indicate that a methanol loading range of 8.4 mL/g to 8.7 mL/g of EX-2 is acceptable to provide exemestane of good purity. From a ranging screening of the EX-4 preparation process a range of 7.5 mL/g to 9.5 mL/g is permissible and each provided a mixture that contained less than 1% EX-3 by HPLC area.

Potassium hydroxide ratios of 1.05 and 1.3 equivalents were chosen as the verification for the preparation of exemestane from intermediate 5 as the operating parameters are currently 1.1 to 1.2 equivalents of KOH for each mole of EX-2 used at the start of the process. Using 1.05 equivalents of base provided exemestane in 94% isolated yield and a purity of 99.6% by HPLC area analysis. As a part of the ranging analysis of the EX-3 to exemestane conversion process, 1.3 equivalents base was used to produce exemestane with a purity of 99.1% by HPLC of the reaction mixture.

Ranging experimentation also showed that the reaction to produce exemestane progresses at 25° C., but not at a useful rate. After three to four hours (the typical timeframe for conversion from 5 to 6), HPLC area percent showed 62% EX-3 remaining and 38% exemestane present. Carrying out the elimination at 60° C. had a reaction mixture that contained 0.18% area EX-3 and 0.84% methanol adduct as shown below in Formula (VII).

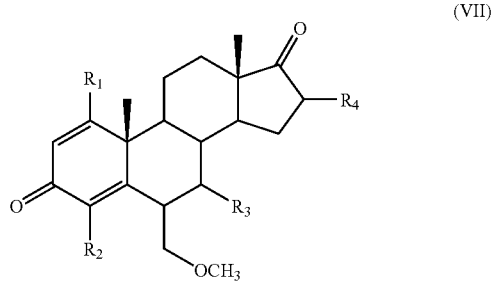

(VII)

Starting material consumption is specified to be less than 1% of intermediate 5 by HPLC area analysis of a reaction aliquot in the exemestane preparation process. An isolation and purification experiment where approximately 4% EX-3 was present in the crude reaction mixture was conducted and the product had 3% area EX-3 present after isolation. Recrystallization afforded the desired steroid exemestane in 83% yield (from EX-3) with a purity of 99.7% by HPLC area (0.22% area EX-3 is present as well).

Solvent exchange from dichloromethane into methanol is monitored by specific gravity for completion of the transfer. The target currently used for the exemestane process is 1.04 g/mL and the range for verification of this part of the synthesis was from 0.791 g/mL (the density of methanol alone) to 1.20 g/mL. The conversion of intermediate 5 to exemestane in methanol with no dichloromethane present is assumed to be the lowest possible specific gravity level possible for the distillation-exchange. In one such case, exemestane was obtained in 88% yield with a purity of 99.4% area by HPLC and 99.1% weight by assay. A higher collected distillate specific gravity endpoint afforded exemestane of excellent quality. A specific gravity of 1.20 g/mL was used as the endpoint and the synthesis afforded exemestane in 94% yield with a purity of 99.5% by HPLC.

Once the level of intermediate 5 drops below 1% area by HPLC, the preparation of exemestane is considered complete and 5.0 to 5.3 mL/g EX-2 water is charged to the reaction mixture to aid in product precipitation/crystallization. A range of 4.5 mL/g to 6.0 mL/g EX-2 of water was probed to determine suitability for use in the solidification process. Utilizing 4.5 mL water/g EX-2 provided 91% exemestane with a purity of 99.4% area. Using 6.0 mL/g for the process produced exemestane with an isolated yield of 85% and purity of 99.5% area after isolation and subsequent recrystallization.

Once the water has been added, the slurry that is obtained is cooled to 10±5° C. and held for a minimum of two hours. Shorter hold times of an hour and as long as 6 hours at 5±5° C. provide product in excellent yield and purities. Holding the methanol/water slurry of exemestane at 0±5° C., after isolation, gave the product in 92% isolated yield with a purity of 99.4%. Without cooling and holding the slurry at 25±5° C. afforded exemestane in 89% yield with an HPLC area purity of 99.4%.

Hold times of one and sixteen hours were investigated for the cooled exemestane slurry to determine the impact of on yield and/or purity. Holding for one hour at 5±5° C. afforded material in 92% isolated yield with a an HPLC area percent of 99.3%. An extended hold of sixteen hours provided 89% exemestane that has a purity of 99.5% by HPLC area.

Recrystallization of wet (50% water by weight) exemestane proceeded to give material in an excellent yield of 93% with a purity of 99.9% HPLC area.

In terms of material quality, the current method for recrystallization for exemestane performs very well. It calls for the use of 10 mL acetonitrile for each gram of crude exemestane, so a range of 9 mL/g up to 15 mL/g was investigated. The experiment with 9 mL acetonitrile gave exemestane with a purity of 99.9% by HPLC analysis and a yield of 94%. Use of 15 mL/g for recrystallization gave a moderately reduced yield 87% and purity of 99.9% for the recovered exemestane.

The recrystallization method also calls for addition of 10 mL water per gram of crude exemestane once a refluxing solution is obtained. There was little difference between the lower and upper ranges for water amounts that were examined. When 9 mL/g water was used, exemestane was obtained in 93% isolated yield with an excellent purity of 99.9% according to HPLC area analysis. With 15 mL/g water, the product was obtained in 95% yield with an HPLC area percent of 99.8.

Drying of exemestane with the current process is done at 80° C., which is required for adequate removal of acetronitrile. Up to 100° C. can be tolerated for 18 hours, as evidenced by holding exemestane in a vacuum oven set to this temperature. This material had a purity of 99.8% HPLC area and recovery of 92%.

Example 4

Discussion

The conversion of EX-2 to EX-3 is an efficient process that usually proceeds quickly using the standard conditions of 1.15 equivalents of methanesulfonyl chloride and 1.3 equivalents of triethylamine. This process requires dry solvents and reagents to ensure good conversion, as methanesulfonyl chloride is moisture sensitive. If conversion is incomplete (more than 1% EX-2 remaining by area), additional methanesulfonyl chloride and/or triethylamine can be added as needed. If the pH of the reaction mixture is acidic, then more triethylamine is required. If the solution is basic (pH>7) and the area percent of EX-2 remains relatively constant, then addition of supplemental methanesulfonyl chloride is required.

Based on ranging studies, the temperature at the start of the addition of methanesulfonyl chloride the EX-2 solution can range from 0 to 35° C. As a safety concern, it is important to avoid a rapid exotherm and possible vigorous refluxing of the reaction mixture (i.e. keep the mixture cool).

Even though there is typically excellent conversion of EX-2 to EX-3, up to 3 weight percent EX-2 can be present as the exemestane isolation and recrystallization process can remove it.

Methanol loadings for the preparation of exemestane can range from 7.5 mL/g up to 9.5 mL/g of EX-2 used in the process. This range adequately covers the current operating range of 8.4 mL/g to 8.7 mL/g of EX-2, providing good quality crude product prior to isolation.

Base stoichiometry from 1.05 to 1.30 equivalents has negligible impact on the quality of exemestane isolated, but higher base loadings are expected to produce more of the methanol adduct of Formula VII more quickly as would higher temperatures. Refluxing the elimination reaction mixture was acceptable in the lab, but close monitoring of reaction progress is critical under these more forcing conditions since the methanol adduct impurity forms during the latter portion of the 5 to 6 conversion process. Over time, conducting the elimination at 28° C. would be expected to convert EX-3 to exemestane, but very slowly.

Specific gravity of collected distillate is also an excellent marker here for determining the endpoint of the removal of dichloromethane and transfer into methanol. A range of 0.791 g/mL to 1.20 g/mL is well-tolerated according to lab experiments.

Water added for precipitation/crystallization the exemestane, as well as removal of water soluble impurities, is well-tolerated for the range of 4.5 to 6.0 mL water per gram of EX-2. The product is obtained in good yields and excellent purities.

There was a very small exemestane yield difference between the cooled and uncooled slurries, and no significant difference in purities of the material isolated (both were 99.4%).

Hold times had negligible impact on yield and purity of exemestane. As a result, hold times of more than one hour at 5±5° C. are not required.

The prior presence of 50% water (by weight with respect to amount of exemestane) does not noticeably impact the dissolution of exemestane in refluxing acetonitrile and has had no impact on yield or purity of the recrystallized product. Drying of the crude exemestane cake is not required, so long as there is not more than 50% weight water present. Additional water may or may not be tolerated during dissolution of exemestane in refluxing acetonitrile.

Recrystallization solvent ratio ranges from nine to fifteen milliliters of acetonitrile and water for each gram of crude exemestane did not impact the yield or purity significantly. There was perhaps a slight drop in yield of isolated exemestane with a higher ratio of acetronitrile used and a small increase with a higher loading of water.

Example 4

Conclusions

The synthesis of exemestane from 6-hydroxymethyl-androsta-1,4-diene-3,17-dione (EX-2) represents a dramatically improved process that does not require the isolation of 6-methanesulfonyloxymethyl-androsta-1,4-diene-3,17-dione (intermediate 5). By avoiding the isolation of EX-3, yield losses are minimized and the process is more time efficient since drying of the organic solution, concentration and isolation of solid EX-3 is not needed.

As outlined, the current process delivers high quality exemestane that after isolation requires only one recrystallization to meet established material specifications. Development of the 1:1 acetonitrile/water system for recrystallization was a significant improvement over previous recrystallization solvent systems. It removes the common, significant impurities such as EX-2, EX-3, ADD and the methanol adduct impurity very effectively.

The ranging studies demonstrated that the process to prepare exemestane via intermediate 5 from EX-2 is a reproducible and reliable process when operating or verification range parameters are adhered to well. Yields are typically around 90% after isolation of exemestane with recrystallization yields also at 90% in most cases. Purities are very good prior to recrystallization from 1:1 ACN/water and excellent following it.

Thus, the invention provides improved methods and intermediates for preparing aromatase inhibitors such as exemestane in high purity and high yield, particularly in commercial quantities.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention relates to methods of making aromatase inhibitors such as exemestane and its intermediates. Exemestane tablets are indicated for the treatment of advanced breast cancer in postmenopausal women whose disease has progressed following tamoxifen therapy.

What is claimed is:

1. A method for preparing a compound of formula (I)

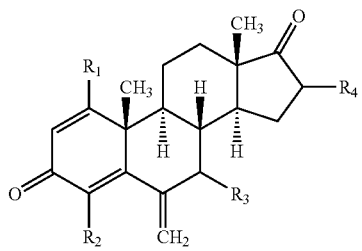

wherein each of $R_1$, $R_2$, $R_3$, $R_4$, independently, is hydrogen, halogen or $C_1$-$C_6$ alkyl, the method comprising:

reacting a compound of formula (II)

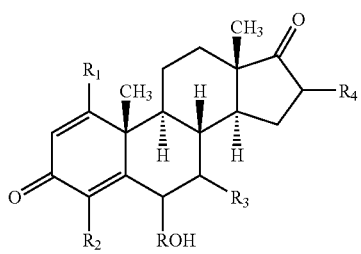

wherein $R_1$, $R_2$, $R_3$, $R_4$ are as defined above and R is alkylene, with a deprotonating agent and a compound of the formula $R_5SO_2X$ wherein $R_5$ is $C_1$-$C_5$ alkyl and X is halogen so as to obtain a compound of formula (III)

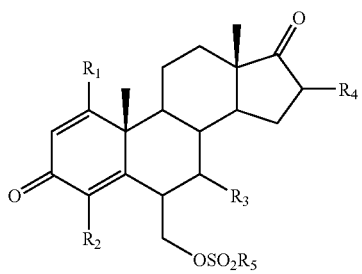

wherein $R_1$, $R_2$, $R_3$, $R_4$, $R_5$ are as defined above; and
reacting the compound of formula (III) with a base.

2. The method of claim 1 wherein:
wherein each of $R_1$, $R_2$, $R_3$, $R_4$ is hydrogen.

3. The method of claim 1 wherein:
R is methylene.

4. The method of claim 1 wherein:
the deprotonating agent is an amine.

5. The method of claim 1 wherein:
the deprotonating agent is a tertiary amine.

6. The method of claim 1 wherein:
the deprotonating agent is a trialkyl amine.

7. The method of claim 1 wherein:
$R_5$ is methyl.

8. The method of claim 1 wherein:
$R_5$ is methyl and X is chlorine.

9. The method of claim 1 wherein:
wherein each of $R_1$, $R_2$, $R_3$, $R_4$ is hydrogen,
R is methylene,
the deprotonating agent is a trialkyl amine,
$R_5$ is methyl, and
X is chlorine.

10. The method of claim 1 wherein:
the base is an alkali metal hydroxide.

11. The method of claim 1 wherein:
the base is potassium hydroxide.

12. The method of claim 1 wherein:
the compound of formula (III) is reacted with the base in a solvent.

13. The method of claim 1 wherein:
the solvent is an alkanol.

14. A method for preparing a compound of formula

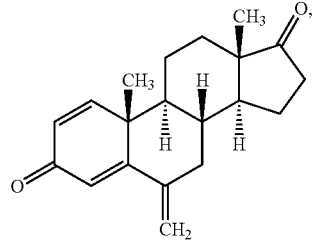

the method comprising:
reacting a compound of formula (V)

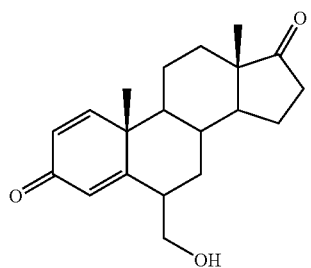

with a deprotonating agent and a compound of the formula $R_5SO_2X$ wherein $R_5$ is $C_1$-$C_5$ alkyl and X is halogen so as to obtain a compound of formula (VI)

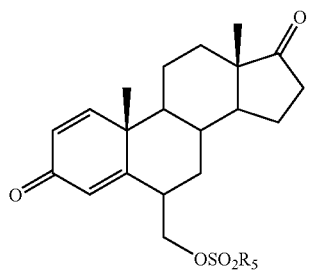

and then reacting the compound of formula (VI) with a base in a solvent.

15. The method of claim 14 wherein:
$R_5$ is methyl and X is chlorine.

16. The method of claim 15 wherein:
the base is an alkali metal hydroxide, and
the solvent is an alkanol.

* * * * *

UNITED STATES PATENT AND TRADEMARK OFFICE
CERTIFICATE OF CORRECTION

PATENT NO.        : 8,183,401 B2
APPLICATION NO.   : 10/586237
DATED             : May 22, 2012
INVENTOR(S)       : Kunnen et al.

It is certified that error appears in the above-identified patent and that said Letters Patent is hereby corrected as shown below:

In the Specifications:

Column 9, Line 15 "lafter" should read -- latter --

Signed and Sealed this
Fourth Day of June, 2013

Teresa Stanek Rea
*Acting Director of the United States Patent and Trademark Office*